(12) United States Patent
Do

(10) Patent No.: US 12,178,394 B2
(45) Date of Patent: Dec. 31, 2024

(54) ENDOSCOPE HEAD COMPRISING A HOUSING ELEMENT MADE FROM TRANSPARENT MATERIAL

(71) Applicant: HOYA CORPORATION, Tokyo (JP)

(72) Inventor: Anh Minh Do, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 336 days.

(21) Appl. No.: 17/282,576

(22) PCT Filed: Oct. 24, 2019

(86) PCT No.: PCT/IB2019/001083
§ 371 (c)(1),
(2) Date: Apr. 2, 2021

(87) PCT Pub. No.: WO2020/084340
PCT Pub. Date: Apr. 30, 2020

(65) Prior Publication Data
US 2021/0338062 A1     Nov. 4, 2021

(30) Foreign Application Priority Data

Oct. 26, 2018   (DE) ...................... 10 2018 126 794.0

(51) Int. Cl.
*A61B 1/00* (2006.01)
*A61B 1/06* (2006.01)

(52) U.S. Cl.
CPC ...... *A61B 1/00135* (2013.01); *A61B 1/00096* (2013.01); *A61B 1/0676* (2013.01)

(58) Field of Classification Search
CPC ............ A61B 1/00135; A61B 1/00096; A61B 1/0676; A61B 1/00137; A61B 1/051; A61B 1/0615; A61B 1/0684; A61B 1/07; A61B 1/00119; A61B 2017/22059; G02B 23/2453; G02B 23/2461; G02B 23/2484
(Continued)

(56) References Cited

U.S. PATENT DOCUMENTS 8,485,966 B2   7/2013   Robertson
9,671,606 B2   6/2017   Fujii
(Continued)

FOREIGN PATENT DOCUMENTS

CN   104856635 A   8/2015
CN   102307510 A   1/2017
(Continued)

OTHER PUBLICATIONS

U.S. Appl. No. 17/284,223 to Anh Minh Do, which was filed Apr. 9, 2021.
(Continued)

*Primary Examiner* — Timothy J Neal
*Assistant Examiner* — James Edward Boice
(74) *Attorney, Agent, or Firm* — GREENBLUM & BERNSTEIN, P.L.C.

(57) ABSTRACT

An endoscope head and endoscope including such endoscope head includes a camera, a housing element made from transparent material which surrounds the camera at least laterally and at least in portions and extends to the distal end of the endoscope head, and including at least one illumination unit which is arranged laterally from the camera and/or proximally from the camera.

15 Claims, 7 Drawing Sheets

(58) Field of Classification Search
USPC .................................................. 600/104, 171
See application file for complete search history.

(56) References Cited

U.S. PATENT DOCUMENTS

| | | | |
|---|---|---|---|
| 2008/0234547 A1* | 9/2008 | Irion .................. | A61B 1/00105 600/146 |
| 2010/0286475 A1 | 11/2010 | Robertson | |
| 2011/0288372 A1 | 11/2011 | Petersen | |
| 2012/0184818 A1* | 7/2012 | Sugisawa ............. | A61B 1/0051 600/121 |
| 2013/0137923 A1 | 3/2013 | Honda et al. | |
| 2013/0281779 A1* | 10/2013 | Robertson ............ | A61B 1/0669 600/109 |
| 2014/0024895 A1 | 1/2014 | Allyn | |
| 2015/0073212 A1* | 3/2015 | Yamazaki ............ | A61B 1/0615 600/179 |
| 2017/0242240 A1* | 8/2017 | Krivopisk .......... | A61B 1/00188 |
| 2017/0245734 A1* | 8/2017 | Kaneko .................. | A61B 1/307 |
| 2018/0008138 A1* | 1/2018 | Thommen .............. | A61B 1/051 |
| 2018/0125343 A1 | 5/2018 | Schostek et al. | |
| 2019/0183325 A1* | 6/2019 | Troller .................. | A61B 1/051 |
| 2019/0246027 A1 | 8/2019 | Kuhn et al. | |
| 2019/0328214 A1 | 10/2019 | Do | |
| 2020/0008659 A1 | 1/2020 | Viebach et al. | |
| 2020/0155190 A1* | 5/2020 | Basadonna ........ | A61B 1/00078 |
| 2020/0178770 A1 | 6/2020 | Do | |

FOREIGN PATENT DOCUMENTS

| | | |
|---|---|---|
| CN | 107105978 A | 8/2017 |
| DE | 10 2016 122 864 A1 | 5/2018 |
| JP | S60-066223 A | 4/1985 |
| JP | S60-069619 A | 4/1985 |
| JP | 2002-051971 A | 2/2002 |
| JP | 2002-143083 A | 5/2002 |
| JP | 2002-233494 A | 8/2002 |
| JP | 2005-124776 A | 5/2005 |
| JP | 2009-207578 A | 9/2009 |
| JP | 2012-090723 A | 5/2012 |
| JP | 2015-077400 A | 4/2015 |
| WO | WO 2012/137737 A1 | 10/2012 |
| WO | WO 2012/170401 A2 | 12/2012 |
| WO | WO 2015/056106 A2 | 4/2015 |
| WO | WO 2016/181724 A1 | 11/2016 |
| WO | WO 2018/087227 A1 | 5/2018 |

OTHER PUBLICATIONS

U.S. Appl. No. 17/281,429 to Anh Minh Do, which was filed Mar. 30, 2021.

International Search Report issued in International Bureau of WIPO Patent Application No. PCT/IB2019/001083, dated Dec. 20, 2019, along with an English translation thereof.

Written Opinion issued in International Bureau of WIPO Patent Application No. PCT/IB2019/001083, dated Dec. 20, 2019, along with an English translation thereof.

Office Action issued in Chinese Patent Application No. 201980069875.8, dated Mar. 31, 2023.

Office Action issued in Japanese Patent Application No. 2021-522999, dated Aug. 22, 2023, together with an English-language translation.

Decision to Grant a Patent issued in Japanese Patent Application No. 2021-522999, dated Dec. 19, 2023.

Search Report issued in European patent application No. 19797359.7, dated Jul. 2, 2024.

* cited by examiner

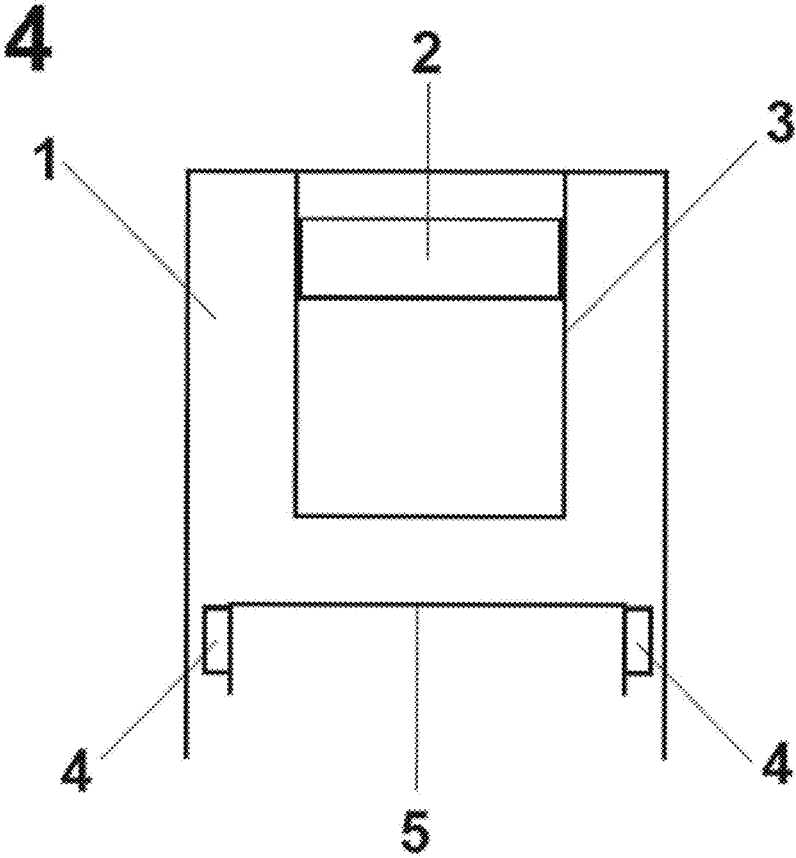
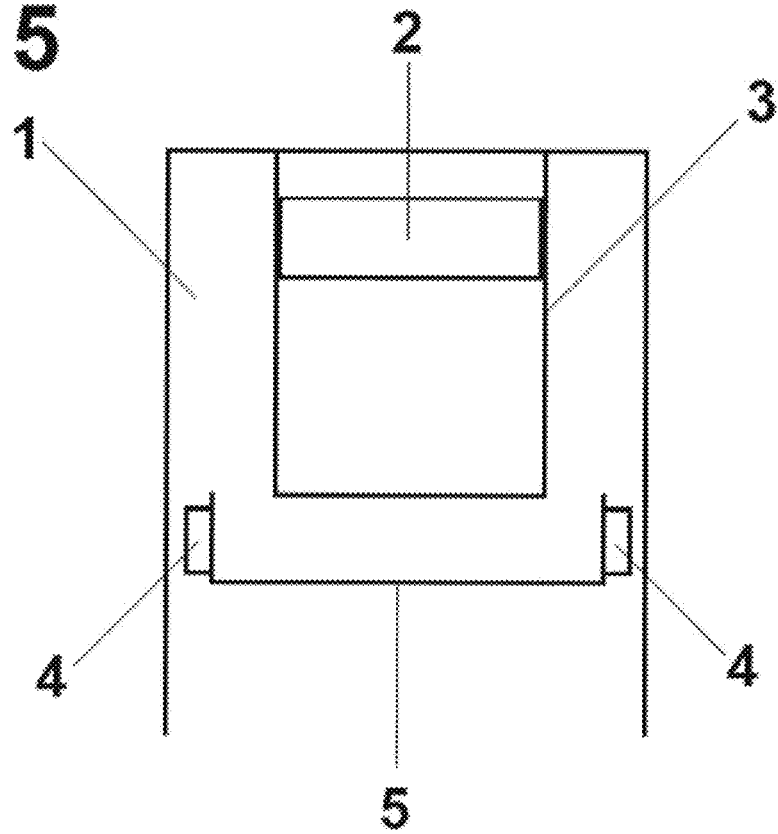

ENDOSCOPE HEAD COMPRISING A HOUSING ELEMENT MADE FROM TRANSPARENT MATERIAL

The present invention relates to an endoscope head comprising a housing element in which a camera and an illumination unit are accommodated.

In a known endoscope, a camera and an illumination unit for illumination and for image-taking of a region to be viewed by the endoscope are disposed at the distal end of the endoscope head.

Due to the small size, it is always necessary in an endoscope head to save space so that the required components can be advantageously accommodated in a confined space.

Hence, it is the object of the invention to provide an endoscope head in which a camera and an illumination unit are advantageously installed and a favorable transmission of light from the illumination unit is possible.

This object is achieved by an endoscope head comprising the features of claim 1.

Advantageous developments are the subject matter of the dependent claims.

The invention thus relates to an endoscope head comprising a camera, a housing element made from transparent material which surrounds the camera at least laterally and at least in portions and extends to the distal end of the endoscope head, and comprising at least one illumination unit which is disposed laterally from the camera and/or proximally from the camera.

The illumination unit emits light in such a manner that the light propagates through the material of the transparent housing element. In this way, the housing element acts as a light guide. The light of the illumination unit is emitted through the housing element to the regions outside the endoscope head. Thereby, the light of the illumination unit can be emitted past the camera through the housing element to the outside. The scenery illuminated there outside the endoscope head is recorded by the camera.

In accordance with the invention, a comprehensive potential (capability) is resulting with respect to the space-saving arrangement of the components of the endoscope head and with respect to the light being guided and propagating from the illumination unit to the outside, which takes place within the housing element. Specific examples will be shown hereinafter and in the embodiments.

In the endoscope head, the at least one illumination unit may be arranged directly behind the camera, when viewed from the distal side. The space forming laterally from the camera, when viewed in the longitudinal direction of the endoscope head, may be used as light guide or for other components of the endoscope head. This helps materialize an especially slender endoscope head. Light can be emitted by the illumination unit through the transparent housing element past the camera in the distal direction and toward the lateral direction.

The at least one illumination unit can be arranged radially on the side of the camera. Thus, the light can be guided in the distal direction through the material of the transparent housing element. The light propagation is not obstructed.

The at least one illumination unit can be spaced apart from the outer periphery of the housing element. The illumination unit can be disposed either within the housing element or at the distal edge of the housing element. This ensures the illumination unit to emit light even in the radial (lateral) direction through the material of the transparent housing element.

The at least one illumination unit may be aligned so that it irradiates light in the distal direction. Alternatively, the at least one illumination unit may be aligned so that it irradiates light in the radial direction. In another alternative, both possibilities, i.e., an illumination unit aligned in the distal direction (pointing to the distal direction) and an illumination unit aligned in the radial (lateral) direction (pointing to the radial direction), may be combined.

Proximally from the illumination unit, a light reflector may be arranged in the endoscope head such that it reflects light from the illumination unit in the distal direction. Thus, even light from an illumination unit which initially propagates in the distal direction of the endoscope head and then is reflected by the light reflector toward the distal side can be guided through the material of the transparent housing element.

The camera may be surrounded by a sleeve body so that—when viewed in the lateral direction—the sleeve body is disposed between the camera and the housing element, the sleeve body shielding and retaining the camera, and the camera being aligned in the distal direction. Thus, the camera is protected and shielded by the sleeve body.

The housing element can be made from transparent plastic material or glass. This ensures advantageous propagation of the light within the transparent housing element. Ideally, no clouding is present in the material of the transparent housing element. The material of the transparent housing element preferably is neither milky nor cloudy.

The endoscope head may include a channel component disposed at a lateral portion of the camera. A compact structure in which the channel component and the camera (with or without its surrounding sleeve body) are arranged as closely as possible to each other is feasible. In this way, the components provided in the endoscope head (such as the channel component and the camera) which are not capable of guiding light can be concentrated and the remaining space is available for the material of the transparent housing element for the light transmission.

The housing element may fill the space between the sleeve body and the outer periphery of the endoscope head. Thus, the space between the sleeve body and the outer periphery of the endoscope head is transparent and can be utilized for the light transmission.

Channel elements may be incorporated in the sleeve body. In this way, components (such as channel elements) which cannot guide light are transferred into the sleeve body which cannot guide light anyway, either, so that more space is available for the material of the transparent housing element for the light transmission.

In the housing element, at least one light forming element may be formed integrally at a predetermined portion. Alternatively, in the housing element at least one light forming element may be embedded as a separate element at a predetermined portion. Thus, a portion within the housing element can be utilized to specifically form light emitted by the illumination unit. Accordingly, light forming is not restricted. Any suitable light forming elements may be utilized in appropriate numbers and at appropriate positions in the housing element. In this way, light can be specifically passed by regions which are not available for the light transmission, such as the components which cannot guide light, and/or can be guided to desired locations inside the endoscope head or outside the endoscope head.

The light forming element of the housing element may be configured so that a portion of the housing element is lens-shaped. Any further shapes of a light forming element may be applied. The shape of the light forming element may be formed by compacting the material of the housing element within the housing element.

The light forming element of the housing element may be disposed adjacent to at least one illumination unit. The distance of the light forming element from the illumination unit may be appropriately selected.

The housing element may include a portion that covers the camera on the distal side. Thus, transparent material is provided at the camera port. The camera thus has a transparent light admission cover. Said light admission cover is formed integrally with the remaining housing element.

An endoscope may be provided with an endoscope head according to any one of the above-discussed aspects. Such endoscope may be a rigid or a flexible endoscope. The invention is applicable to any type of endoscope.

The afore-explained aspects of the present invention may be adequately combined.

BRIEF DESCRIPTION OF THE DRAWING

FIG. 4 shows a schematic side view of an endoscope head of a second embodiment.

FIG. 5 shows a schematic side view of an endoscope head of a third embodiment.

Hereinafter, the present invention will be described in detail with reference to the drawings by way of embodiments.

FIRST EMBODIMENT

In the following, a first embodiment of the present invention will be described with reference to FIGS. 1 to 3.

Figure 1:
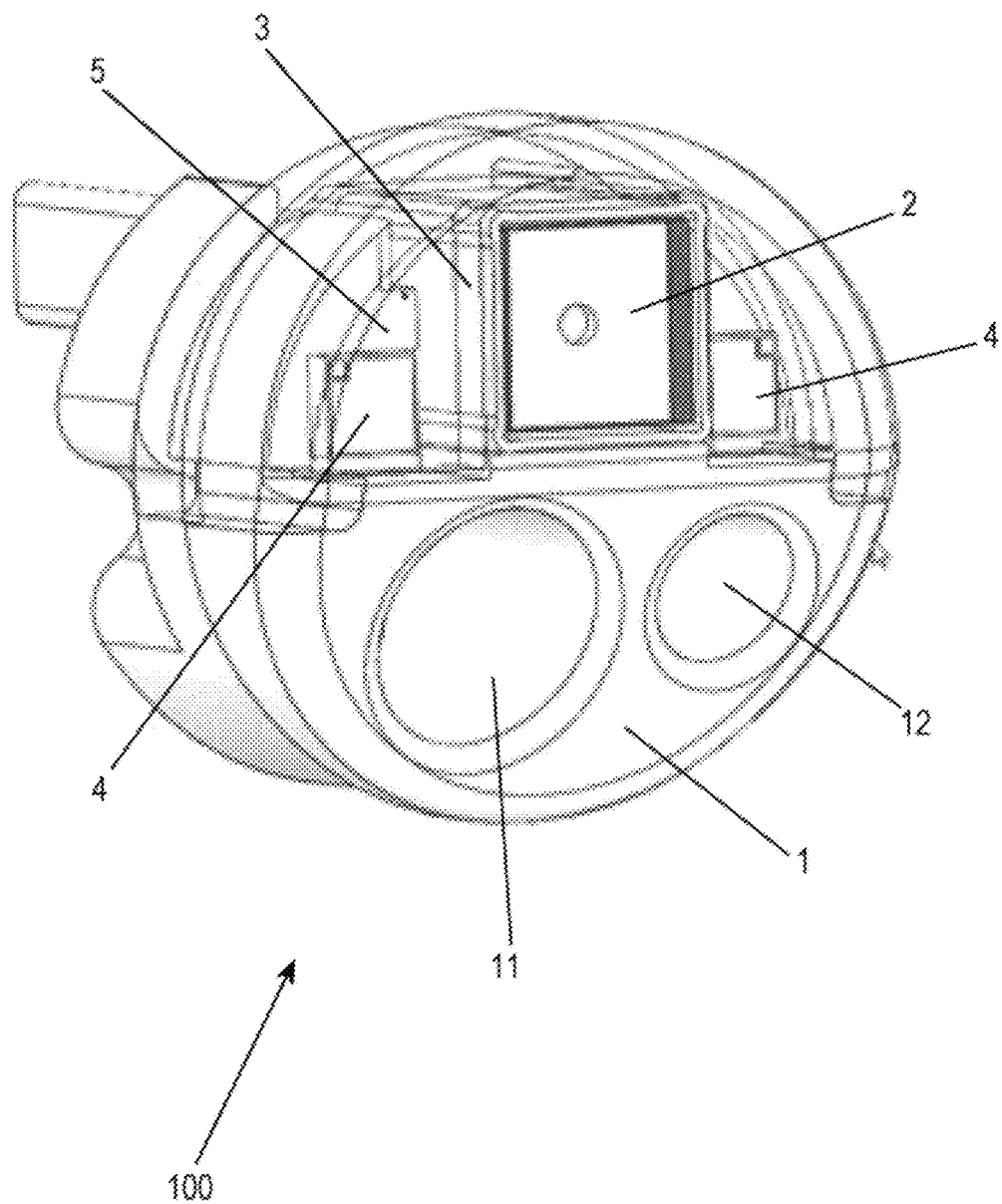
FIG. 1 shows a schematic perspective view of an endoscope head of a first embodiment of the present invention.

FIG. 1 illustrates a perspective view of an endoscope head 100 of the first embodiment. In particular, the distal end of the endoscope head 100 is shown in a perspective view.

An endoscope according to the invention includes the endoscope head 100 on the distal side. The endoscope head 100 according to the invention has a cylindrical shape. The endoscope head 100 includes a housing element 1 made from transparent material. The housing element 1 is a transparent body. In the housing element 1, a camera 2 surrounded by a camera sleeve 3 is disposed. A first LED 4 and a second LED 4 are arranged on a printed circuit board 5 adjacent to the camera. Further, a working channel 11 and a flushing channel 12 extend through the housing element 1 in the axial direction of the endoscope head.

The camera 2 is arranged in the camera sleeve 2 in a known manner so that the camera sleeve 3 surrounds the camera 2. The camera faces the distal side of the endoscope head. A distal end portion of the camera sleeve 3 protrudes from the camera 2 in the distal direction. In this way, lateral light is shielded from being incident on the camera 2 by the distal end portion of the camera sleeve 3. The camera sleeve 3 preferably is a square tubular section extending in the longitudinal direction of the endoscope head. The camera 2 is embedded in the camera sleeve 3.

The housing element 1 surrounds the camera sleeve 3. More exactly speaking, the camera sleeve 3 is surrounded, on its lateral side and its proximal side, by the housing element 1. Merely on the distal side, the camera sleeve 3 is not covered by the housing element 1. The printed circuit board 5 is disposed on the proximal side of the proximal end of the camera sleeve 3. On the printed circuit board 5, the two LEDs 4 are arranged so that they are placed laterally from the camera sleeve 5 but proximally from the camera sleeve 3. The printed circuit board 5 may be spaced apart from the proximal end of the camera sleeve 3. As an alternative, the printed circuit board 5 may abut on or be in contact with the proximal end of the camera sleeve 3.

Moreover, the working channel 11 and the flushing channel 12 are arranged in the housing element 1 in the axial direction such that said channels 11 and 12 extend in parallel to the direction of extension of the camera sleeve 3. The endoscope head 100 according to the invention includes the working channel 11 and the flushing channel 12 which extend along the longitudinal direction of the endoscope head 100 and in parallel to each other.

The housing element 1 is made from transparent plastic material or glass. The housing element 1 is a solid body. For example, the housing element 1 may be manufactured by any casting process (such as injection molding) in a specifically designed mold.

The housing element 1 forms a cylindrical body extending in the longitudinal direction of the endoscope head, as shown in FIG. 1. In the housing element 1, the camera sleeve 3, the printed circuit board 5 including the LEDs 4, the working channel 11 and the flushing channel 12 are arranged so that they are spaced apart from the outer periphery of the cylindrical housing element.

In the housing element 1, the LEDs 4 are disposed so that at least to the distal side they abut merely on the material of the housing body 1.

Each of the working channel 11 and the flushing channel 12 is configured in the housing element 1 such that the inner peripheral wall of the working channel 11 and the inner peripheral wall of the flushing channel 12 are formed by the housing element 1.

Figure 2:
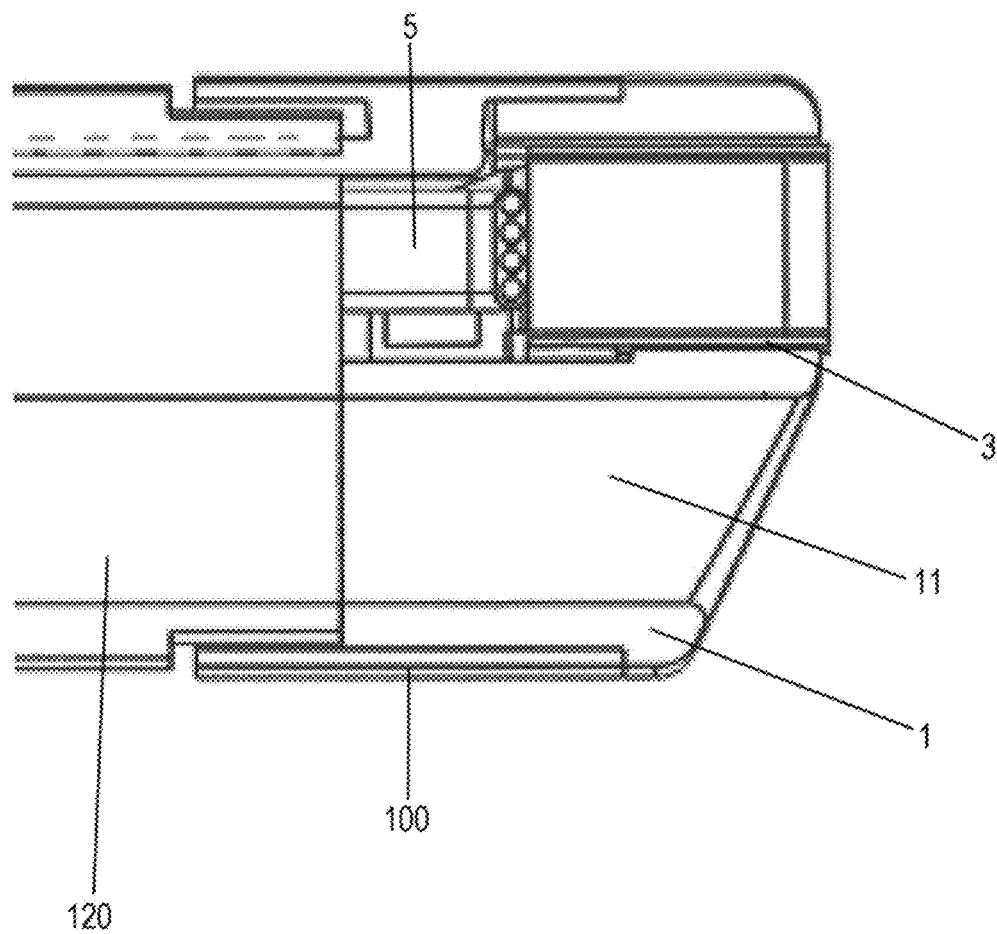
FIG. 2 shows a schematic side view of the endoscope head from FIG. 1.

FIG. 2 illustrates a schematic side view of the endoscope head from FIG. 1. Especially, FIG. 2 shows a schematic side view of the endoscope head from the left side in FIG. 1.

As illustrated in FIG. 2, the endoscope head 100 is located at the distal end of an insertion tube 120. The working channel 11, the flushing channel 12 (not shown in FIG. 2) and an electric connection for the printed circuit board 5 including the LEDs 4 (not shown in FIG. 2) extend from the proximal side. The camera sleeve 3 is surrounded by the material of the housing body 1.

Figure 3:
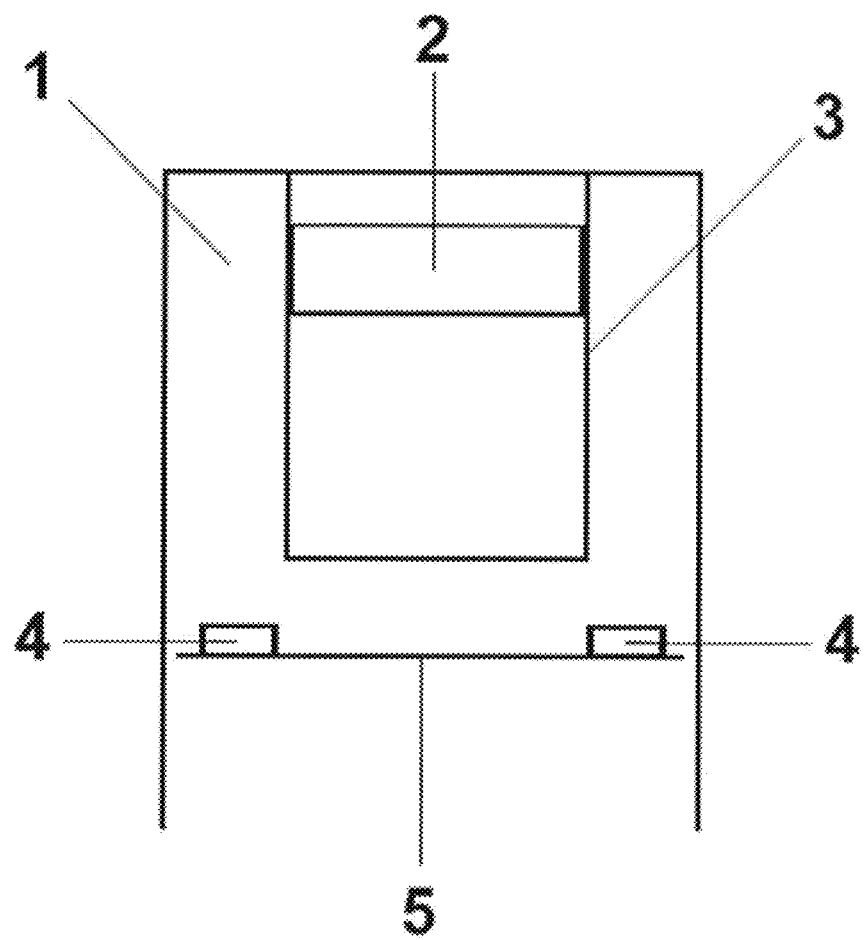
FIG. 3 shows a schematic side view of the endoscope head from FIG. 1.

FIG. 3 illustrates a schematic side view of the endoscope head from FIG. 1. In particular, FIG. 3 shows a schematic side view of the endoscope head from FIG. 1 from the top.

As illustrated in FIG. 2, the two LEDs 4 are disposed on the printed circuit board 5 so that they point to the distal direction. The two LEDs 4 thus emit light mainly in the distal direction. The light emitted by the LEDs 4 passes through the transparent housing element 1. The material and the design of the housing element 1 are selected such that the light propagates preferably unhindered within the housing element 1. Preferably, the material of the housing element 1 is not milky and has no clouding, either. The light emitted by the LEDs 4 therefore irradiates the region outside the housing element 1 which is distal and lateral from the LEDs 4.

EFFECT OF THE EMBODIMENT

In the endoscope head 100 according to the invention, the LED 4 emits light for the purpose of illuminating a scenery to be viewed outside the endoscope head 100. The light emitted by the LED 4 passes through the transparent housing element 1 and emerges from the housing element 1. As the housing element 1 is transparent, the housing element 1 acts as a light guide. The propagation of the light within the housing element 1 is not obstructed by the housing element 1 itself. Efficient light emission is thus ensured. Similar effects are also resulting from the further embodiments which will be discussed below.

SECOND EMBODIMENT

Hereinafter, a second embodiment of the present invention will be described with reference to FIG. 4.

FIG. 4 illustrates a schematic side view of the endoscope head of the second embodiment. The second embodiment differs from the first embodiment by the arrangement of the LEDs 4. The remaining structure is equal to that of the first embodiment and therefore will not be repeatedly described.

In the second embodiment, the printed circuit board 5 is folded in the proximal direction at its radial end sides where the LEDs 4 are arranged. The LEDs 4 are arranged on the printed circuit board 5 so that they point to the lateral direction. Thus, the two LEDs 4 emit light basically in the lateral direction. In other words, mainly the radial area of the endoscope head irradiated. The light of the LEDs 4 may emerge unhindered between the LEDs 4 and the outer periphery of the housing element 1.

The light emitted by the LEDs 4 passes unhindered through the transparent housing element 1. Therefore, the light emitted by the LEDs 4 irradiates the region outside the housing element 1 that is located on the distal and proximal sides of the LEDs 4.

THIRD EMBODIMENT

Hereinafter, a third embodiment of the present invention will be described with reference to FIG. 5.

FIG. 5 illustrates a schematic side view of the endoscope head of the third embodiment. The third embodiment differs from the second embodiment by the structure of the printed circuit board and by the arrangement of the LEDs 4. The remaining structure is equal to that of the first and second embodiments and therefore shall not be repeatedly described.

In the third embodiment, the printed circuit board 5 is folded in the distal direction at its radial end sides where the LEDs 4 are disposed. In this example, too, the LEDs 4 are disposed on the printed circuit board 5 such that they point to the lateral direction. Thus, the two LEDs 4 emit light basically in the lateral direction. Therefore, mainly the radial region of the endoscope head is irradiated.

The light emitted by the LEDs 4 passes through the transparent housing element 1. The light emitted by the LEDs therefore irradiates unhindered the region outside the housing element 1 that is located on the distal and proximal sides of the LEDs 4.

FOURTH EMBODIMENT

Hereinafter, a fourth embodiment of the present invention will be described with reference to FIG. 6.

Figure 6:
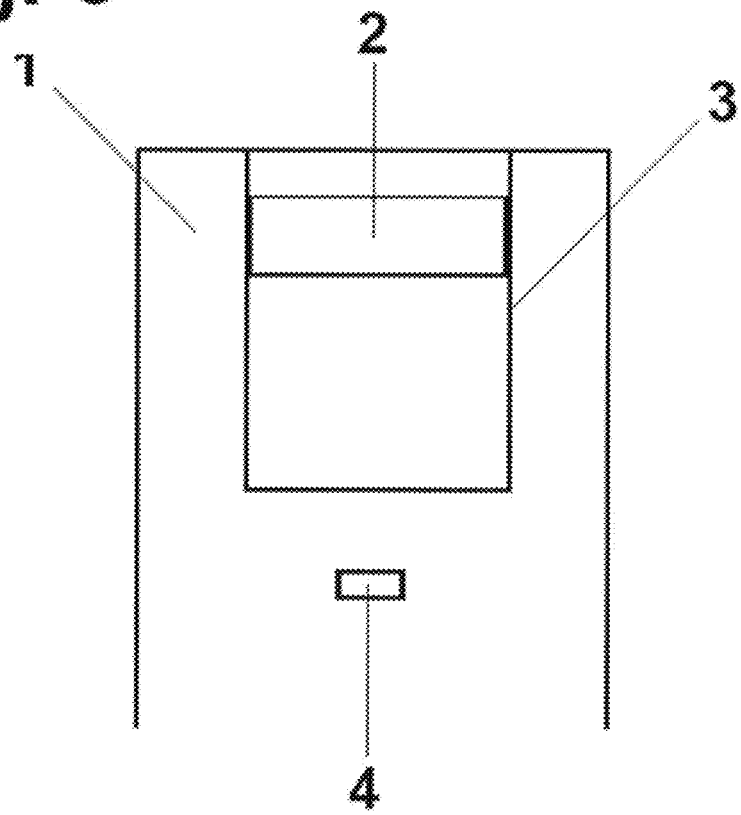
FIG. 6 shows a schematic side view of an endoscope head of a fourth embodiment.

FIG. 6 illustrates a schematic side view of the endoscope head of the fourth embodiment. The fourth embodiment differs from the first embodiment by the LED arrangement. The remaining structure is equal to that of the first embodiment and therefore shall not be repeatedly described.

In the fourth embodiment, the LED 4 is arranged as a single LED or as a group of plural LEDs directly behind the camera sleeve 3, when viewed from the distal side of the endoscope head. The LED 4 may abut on, be in contact with or be somewhat spaced apart from the camera sleeve 3.

When the LED 4 is somewhat spaced apart from the camera sleeve 3, the LED 4 is disposed so that it emits light basically in the distal direction. In so doing, the light is transmitted in the transparent housing element 1. The light propagates in the transparent housing element 1 and irradiates regions distally and radially (i.e., laterally) from the endoscope head.

Alternatively, the LED 4 may be arranged so that it emits light basically in the lateral direction. Thus, mainly the radial region of the endoscope head is irradiated.

In another alternative of the fourth embodiment, the LED 4 or LEDs 4 emit(s) light in the distal direction and in the lateral direction.

FIFTH EMBODIMENT

Hereinafter, a fifth embodiment of the present invention shall be described with reference to FIG. 7.

Figure 7:
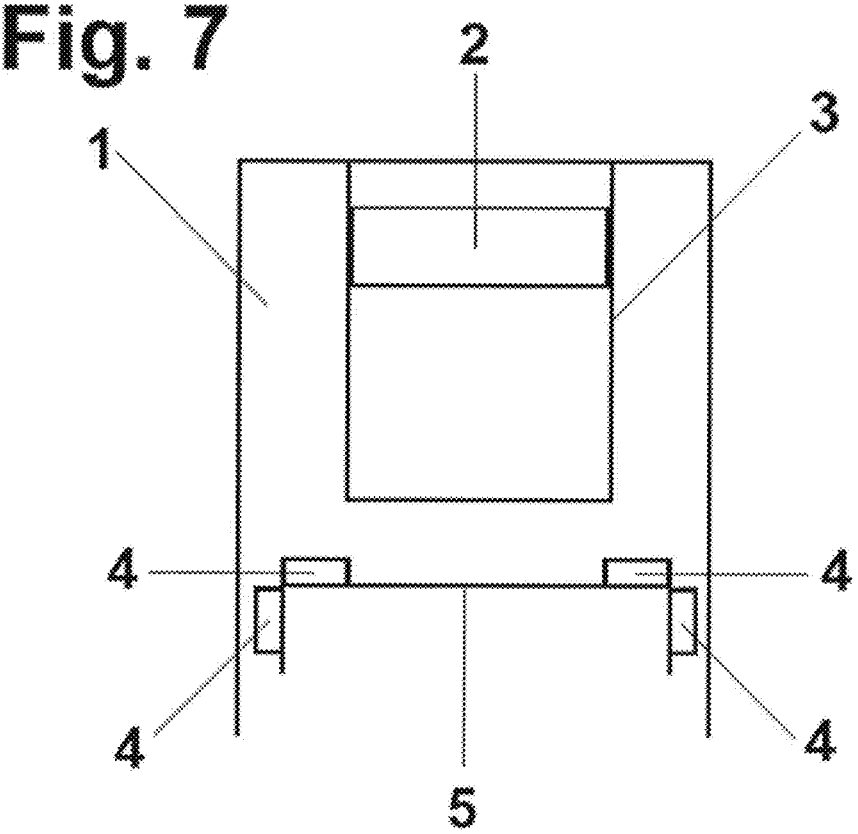
FIG. 7 shows a schematic side view of an endoscope head of a fifth embodiment.

FIG. 7 illustrates a schematic side view of the endoscope head of the fifth embodiment. With regard to the arrangement of the LEDs 4, the fifth embodiment is a combination of the first and second embodiments. The remaining structure is equal to that of the first embodiment and therefore will not be repeatedly described.

In the fifth embodiment, the printed circuit board 5 is folded in the proximal direction at its radial end sides. At the end portions of the printed circuit board 5 folded in the proximal direction, LEDs 4 are arranged just as in the second embodiment. At the areas of the printed circuit board 5 which is located ahead of the folding of the end portions, when viewed from the central axis of the endoscope head (i.e., from the camera sleeve 3), further LEDs 4 are disposed on the printed circuit board 5 such that they point in the distal direction as in the first embodiment.

Hence, in the fifth embodiment, two LEDs 4 emit light basically in the lateral direction and two further LEDs 4 emit light basically in the distal direction.

The light emitted by the LEDs 4 therefore irradiates the region outside the housing element 1 that is located distally and proximally laterally from the LEDs 4.

SIXTH EMBODIMENT

Hereinafter, a sixth embodiment of the present invention will be described with reference to FIG. 8.

Figure 8:
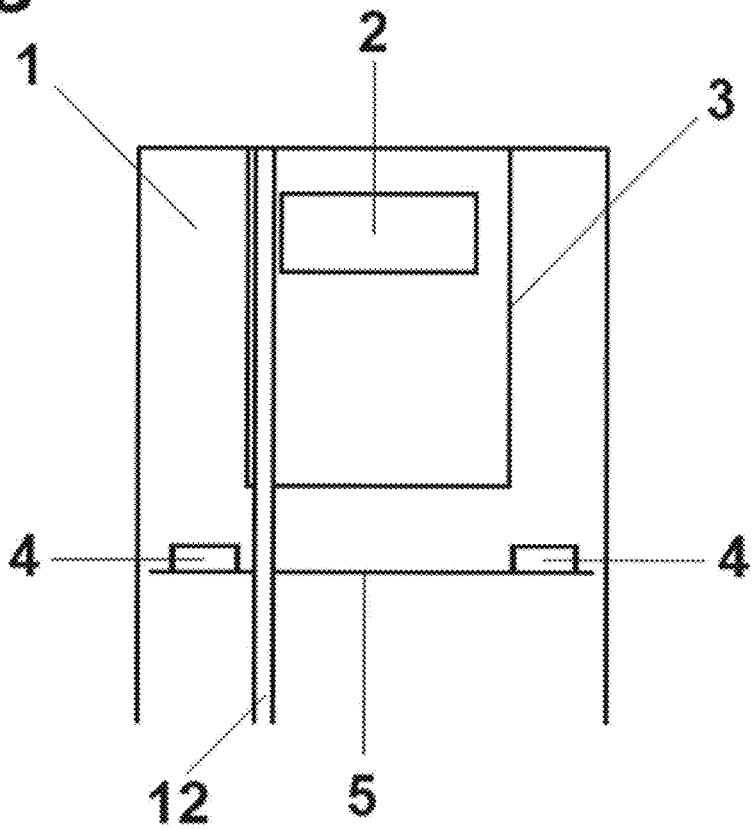
FIG. 8 shows a schematic side view of an endoscope head of a sixth embodiment.

FIG. 8 illustrates a schematic side view of the endoscope head of the sixth embodiment. The sixth embodiment differs from the first embodiment by the structure of the camera 2 and the camera sleeve 3 as well as by the arrangement of the flushing channel 12. The remaining structure is equal to that of the first and second embodiments and, therefore, shall not be repeatedly described.

In the sixth embodiment, the camera 2 is disposed in the camera sleeve 3 so that it is spaced apart from the camera sleeve 3 on at least one side. Accordingly, the camera 2 may be arranged as a single element in the camera sleeve 3. Alternatively, the camera 2 may be arranged to be embedded into a camera sleeve body (not shown) in the camera sleeve 3 such that the camera sleeve body (not shown) extends in parallel to the camera sleeve 3. In this case, the camera sleeve 3 surrounds the camera sleeve body in which the camera 2 is disposed.

In the camera sleeve 3, the flushing channel 12 is disposed as a channel component between the inner wall of the camera sleeve 3 and the camera 2. The flushing channel 12 extends in parallel to the camera sleeve 3.

In the sixth embodiment, the flushing channel 12 is disposed in the camera sleeve 3. Thus, in the region where the LEDs 4 emit light in the lateral and distal directions, the housing element 1 is not provided with the flushing channel 12. Consequently, in the sixth embodiment, fewer elements which may impair the light propagation in the housing element 1 are disposed in the housing element 1.

SEVENTH EMBODIMENT

Hereinafter, a seventh embodiment of the present invention will be described with reference to FIG. 9.

Figure 9:
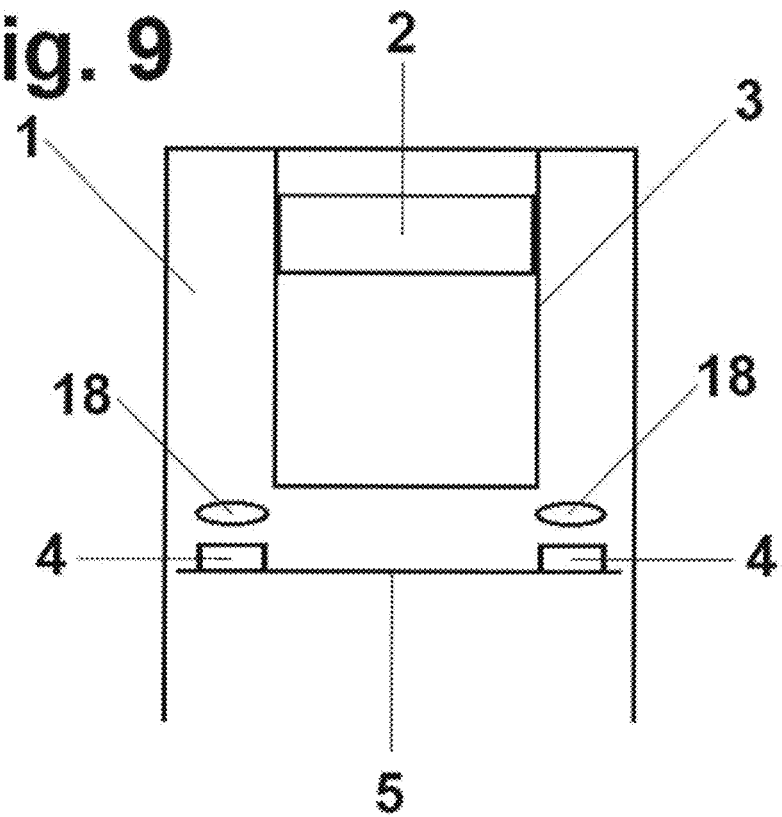
FIG. 9 shows a schematic side view of an endoscope head of a seventh embodiment.

FIG. 9 illustrates a schematic side view of the endoscope head of the seventh embodiment. The seventh embodiment differs from the first embodiment by the fact that optical lenses 18 are disposed in the housing element 1. The remaining structure is equal to that of the first and second embodiments and therefore shall not be repeatedly described.

The optical lenses 18 serve as light forming elements. The optical lenses 18 are disposed close to the light emission regions of the LEDs 4. Thus, the optical lenses 18 are capable of scattering the light emitted by the LEDs 4. In this way, the light emitting angle of the LEDs 4 which an optical lens 18 is assigned to can be increased.

The optical lenses 18 may be embedded as pre-fabricated lenses into the material of the housing element 1 during manufacture of the housing element 1.

In another variant, the optical lenses 18 are formed integrally in the material of the housing element 1 at a predetermined portion from the material of the housing element 1 itself. For this, a mold having openings on the distal side is used. In the openings movable punches are located which can be inserted from outside into the openings and on the inner face include the counterpart to the lens to be formed. The mold is filled with the material forming the housing element 1. Before said material cools, the punch is moved in to compact the poured material of the housing element 1. In this way, the material of the housing element 1 is compressed to form a lens. Then, the material of the housing element 1 may cure. The resulting openings on the distal side of the housing element 1 which have served for producing the lenses may be left as they are. Alternatively, they can be supplemented by the material of the housing element 1 before curing.

Since, in the seventh embodiment, the optical lenses 18 are arranged to be associated with the LEDs 4 at predetermined regions, the light of the LEDs 4 can be better emitted into the housing element 1 and out of the housing element 1.

Light forming elements other than lenses can be applied. Any type of light forming such as light bundling, light scattering, light refraction etc. can be brought about by specific elements provided integrally in the housing element 1 or as separate embedded elements.

EIGHTH EMBODIMENT

Hereinafter, an eighth embodiment of the present invention will be described with reference to FIG. 10.

Figure 10:
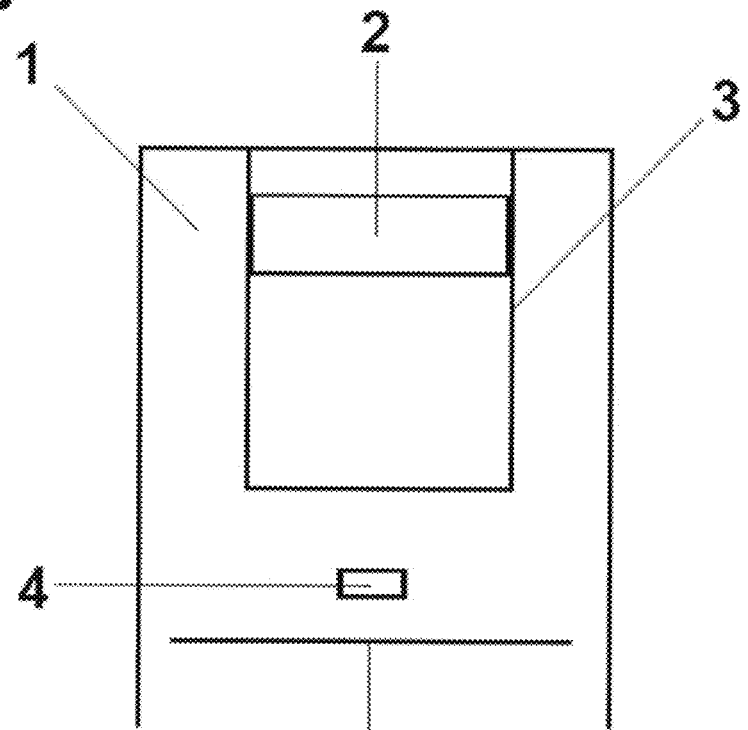
FIG. 10 shows a schematic side view of an endoscope head of an eighth embodiment.

FIG. 10 illustrates a schematic side view of the endoscope head of the eighth embodiment. The eighth embodiment differs from the fourth embodiment by the fact that a reflector 19 is disposed in the housing element 1 or at the proximal edge of the housing element 1. The remaining structure is equal to that of the fourth embodiment and therefore shall not be repeatedly described.

The reflector 19 may be applied as a reflecting layer to the edge of the housing element 1. Alternatively, the reflector 19 may be embedded as a reflecting body in the housing element 1.

The reflector 19 is preferably arranged on the side proximal to the LED 4.

In the eighth embodiment, the LED 4 can be arranged such that it emits light to the proximal side.

Accordingly, the light can be emitted from the LED 4 to the proximal side toward the reflector 19 and can be reflected by the reflector 19 to the distal side. The light emission through the material of the housing element 1 to the distal side can be improved by the reflector 19.

NINTH EMBODIMENT

Hereinafter, a ninth embodiment of the present invention will be described with reference to FIG. 11.

Figure 11:
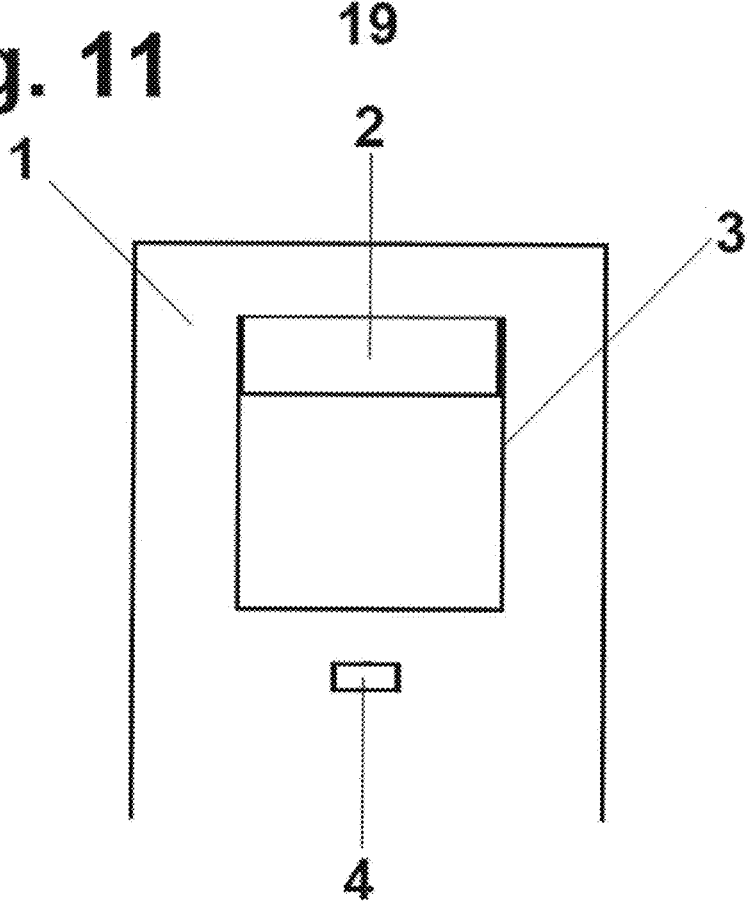
FIG. 11 shows a schematic side view of an endoscope head of a ninth embodiment.

FIG. 11 illustrates a schematic side view of the endoscope head of the ninth embodiment. The ninth embodiment differs from the fourth embodiment by the fact that the distal side of the camera sleeve 3 and of the camera 2 is covered by a portion of the housing element 1. The remaining structure is equal to that of the fourth embodiment and therefore shall not be repeatedly described.

The distal side of the camera sleeve 3 and of the camera 2 is covered by the material of the housing element 1. The material of the housing element 1 is transparent. The region distal from the camera 2 acts as a transparent camera cover. Said transparent camera cover is integral with the remaining housing element 1. Thus, image information of the viewed scenery to be recorded can enter from outside through the material of the housing element 1 to the camera 2.

ALTERNATIVES

The illustrated embodiments may be appropriately combined, unless any technical contradiction is resulting therefrom. To mention just one example, one or more reflectors 19 may be used in each embodiment. Plural reflectors 19 may be arranged at different suitable positions in or at the housing element 1.

The number of the LEDs 4 is not limited. One LED 4 or a plurality of LEDs 4 may be used.

The printed circuit board 5 may be omitted. In this case, the LEDs 4 can be separately controlled.

The LED 4 of the embodiment is merely one example of an illumination unit. Instead of the LED 4, also a light fiber can be used as illumination unit.

In several embodiments, such as, e.g., in the first, second and third embodiments, two respective LEDs 4 are shown in a sectional view of the endoscope head. The respective sectional view in each embodiment corresponds to a top view taking FIG. 1 into account. The invention is not limited thereto. LEDs 4 can be arranged to surround the camera sleeve 3 at any suitable positions within the housing element 1 or can be arranged proximally from the housing element 1.

In the sixth embodiment, the flushing channel 12 is disposed in the camera sleeve 3. Alternatively, the working channel 11 can be disposed, instead of the flushing channel 12 or in addition to the flushing channel 12, in the camera sleeve 3. In this way, even fewer elements which may impair the light propagation within the housing element 1 are arranged in the housing element 1.

The light forming elements of the seventh embodiment may also be applied to the other embodiments. In particular, for the light propagation in the fourth embodiment, light forming elements can be advantageously used to allow light from the LED 4 arranged behind the camera sleeve 3, when viewed from the distal side, to reach the distal side.

By various measures known to those skilled in the art (such as reflectors, light forming elements, etc.) light can be diverted, concentrated, reflected, scattered or intensified within the housing element 1.

LIST OF REFERENCE NUMERALS

1 housing element
2 camera
3 camera sleeve
4 LED
5 printed circuit board
11 working channel
12 flushing channel
18 optical lens
19 reflector
100 endoscope head
120 insertion tube

The invention claimed is:

1. An endoscope head comprising
a camera having a plurality of lenses;
a sleeve surrounding and distally protruding from the plurality of camera lenses;
a transparent housing which surrounds the camera at least laterally and extends to a distal end of the endoscope head;
at least one light emitter disposed laterally from the camera and/or proximally from to the camera sleeve, and further entirely disposed in an upper half of the transparent housing; and
a channel that is entirely disposed in a lower half of the transparent housing, wherein:
the at least one light emitter is positioned so that it emits light through the housing in one of a distal direction or a radial direction, and
the camera is entirely disposed in the upper half of the transparent housing.

2. The endoscope head according to claim 1, wherein the at least one light emitter is disposed directly behind the camera when viewed from distal side of the endoscope head.

3. The endoscope head according to claim 1, wherein the at least one light emitter is disposed radially on a side of the camera.

4. The endoscope head according to claim 1, wherein the at least one light emitter is spaced apart from an outer periphery of the housing element.

5. The endoscope head according to claim 1, wherein a light reflector is disposed in the endoscope head proximally from the at least one light emitter such that it reflects light from the at least one light emitter in the distal direction.

6. The endoscope head according to claim 1, wherein the camera is surrounded by the sleeve so that-when viewed in the lateral direction—the sleeve is arranged between the camera and the housing, the sleeve shielding and retaining the camera, and the camera being aligned in the distal direction.

7. The endoscope head according to claim 6, wherein the housing fills a space between the sleeve and the outer periphery of the endoscope head.

8. The endoscope head according to claim 7, wherein channels are incorporated in the sleeve.

9. The endoscope head according to claim 1, wherein the housing is made from transparent plastic material or glass.

10. The endoscope head according to claim 1, wherein at least one light forming element is formed integrally at a predetermined portion on the housing.

11. The endoscope head according to claim 10, wherein the light forming element of the housing is configured such that a portion of the housing is lens-shaped.

12. The endoscope head according to claim 10, wherein the light forming element of the housing is arranged adjacent to the at least one light emitter.

13. The endoscope head according to claim 1, wherein the housing includes a portion that covers the camera on a distal side.

14. An endoscope comprising an endoscope head according to claim 1.

15. The endoscope head according to claim 1, wherein the at least one light emitter is disposed outside the sleeve.

* * * * *